US012575956B2

(12) United States Patent (10) Patent No.: US 12,575,956 B2
Heinzelmann (45) Date of Patent: Mar. 17, 2026

(54) LIFTING AID AND RIGID BACK ELEMENT

(71) Applicant: Dominik Heinzelmann, Freudenstadt (DE)

(72) Inventor: Dominik Heinzelmann, Freudenstadt (DE)

( * ) Notice: Subject to any disclaimer, the term of this patent is extended or adjusted under 35 U.S.C. 154(b) by 246 days.

(21) Appl. No.: 18/253,512

(22) PCT Filed: Nov. 19, 2021

(86) PCT No.: PCT/DE2021/100921
§ 371 (c)(1),
(2) Date: May 18, 2023

(87) PCT Pub. No.: WO2022/105966
PCT Pub. Date: May 27, 2022

(65) Prior Publication Data
US 2024/0024146 A1 Jan. 25, 2024

(30) Foreign Application Priority Data
Nov. 19, 2020 (DE) ...................... 20 2020 106 6660

(51) Int. Cl.
*A61F 5/28* (2006.01)
*A61F 5/02* (2006.01)
(52) U.S. Cl.
CPC .............. *A61F 5/028* (2013.01); *A61F 5/024* (2013.01)
(58) Field of Classification Search
CPC .......... A61F 5/028; A61F 5/026; A61F 5/024; A61F 5/0104; A61F 5/02; A61F 5/022;
(Continued)

(56) References Cited

U.S. PATENT DOCUMENTS 654,173 A * 7/1900 Mendenhall ............ A61F 5/028
2/44
2,828,737 A * 4/1958 Hale ....................... A61F 5/028
D24/190
(Continued)

FOREIGN PATENT DOCUMENTS

AU 2018256552 A1 5/2019
DE 102004023981 A1 12/2005
(Continued)

*Primary Examiner* — Adam Baker

(74) *Attorney, Agent, or Firm* — Calderon Safran & Wright P.C.; David S. Safran

(57) ABSTRACT

A lifting aid for supporting the trunk muscles, which is arranged in a fixed position on the back of a person carrying it via an upper (wearer) and a lower body connection, having—a fixed back system with the right and left hip elements hinged thereto—at least one mechanical energy storage device which stores energy as elastic deformation and the spring elements of which are attached at one end to the lower body connection; —at least one force transmission element/tensioning device, which is attached to the lower energy storage device(s) and connects it to the back system, as well as freewheel devices with a freewheeling and adjustment function in the hip elements, the fixed back system being fixed to the back and the tensile forces of the energy storage devices being transmitted to the back area, and relates to a fixed back element.

14 Claims, 6 Drawing Sheets

(58) Field of Classification Search
CPC .. A61F 5/03; A61F 5/042; A61F 5/048; A61F
5/37; A61H 3/008; A61H 1/024; A61H
1/0244; A61H 1/0255; A61H 1/0262;
A63B 21/4025
USPC .......................................................... 602/5
See application file for complete search history.

(56) References Cited

U.S. PATENT DOCUMENTS

| | | | | |
|---|---|---|---|---|
| 3,411,500 A * | 11/1968 | Gatts | .................. | A63B 21/4009 |
| | | | | 600/20 |
| 3,436,065 A * | 4/1969 | Flynn | ...................... | F23D 91/02 |
| | | | | 432/9 |
| 2005/0130815 A1 * | 6/2005 | Abdoli-Eramaki | ..... | A61F 5/026 |
| | | | | 482/121 |
| 2013/0090585 A1 * | 4/2013 | Bue, Jr. | .................. | A61F 5/026 |
| | | | | 602/19 |

| | | | | |
|---|---|---|---|---|
| 2014/0207041 A1 * | 7/2014 | Ingimundarson | ..... | A61F 5/0193 |
| | | | | 602/23 |
| 2017/0254531 A1 | 9/2017 | Wahl | | |
| 2018/0272524 A1 | 9/2018 | Ohtsubo et al. | | |
| 2018/0338880 A1 | 11/2018 | Ohta et al. | | |
| 2019/0314542 A1 * | 10/2019 | Ish Cassit | ............. | A61F 5/0104 |
| 2019/0358808 A1 | 11/2019 | Yoshimi et al. | | |
| 2020/0026854 A1 | 1/2020 | Guo et al. | | |
| 2021/0007874 A1 | 1/2021 | Galiana Bujanda et al. | | |
| 2023/0148602 A1 * | 5/2023 | Ikeda | ................... | C07D 249/14 |
| | | | | 504/225 |

FOREIGN PATENT DOCUMENTS

| | | | |
|---|---|---|---|
| DE | 202011104994 U1 | 6/2012 | |
| DE | 102018206782 A1 | 11/2019 | |
| EP | 3176123 A1 | 6/2017 | |
| WO | 2014195373 A1 | 12/2014 | |
| WO | 2020224836 A1 | 11/2020 | |

* cited by examiner

LIFTING AID AND RIGID BACK ELEMENT

BACKGROUND OF THE INVENTION

Field of the Invention

The invention relates to a lifting aid and a fixed back element particularly for use in the same.

Description of the Related Art

The lifting aids for supporting the lifting human are known in a wide variety of forms: They are required for supporting the human strength—for example, as exoskeletons, but also as a mobile carrying support, which—when it is put on by a person carrying it—supports him in his activity. The lifting aids are required in the construction industry, in care facilities, for movers and generally to protect the back. The lifting aids are known, for example, from European Patent Application Publication EP3176123A1, German Patent Application Publication DE102014205200A1 and corresponding US Patent Application Publication US20170254531A1, German Patent Application Publications DE102018206782A1, DE2020111104994U1, DE102004023981A1, or DE102029111718A1, International Patent Application Publication WO 2019161232A1 and corresponding US Patent Application Publication US20210007874A1, and US Patent Application Publication US20200026854A1.

Many known systems were heavy, cumbersome, complex and/or prone to failure and restricted the wearer's natural movement. Others always use an electric motor for support.

The electrically driven lifting supports, in particular, had to be supplied with sufficient electrical power, wherein the motor and power supply additionally increase the weight as well as the effort required to manufacture them—this is especially the case if the drive is to simulate the bending of the wearer.

SUMMARY OF THE INVENTION

It is therefore the object of the invention to propose a simple, mechanical lifting aid.

The object is achieved by a lifting aid comprising a rigid back element 1 for conducting the support forces, which is connected and held between an upper body connection and lower body connections (8, 8.1) and a waist belt 17, wherein at least one first mechanical energy storage device (21, 21.1) for the support is attached to the lower body connection (8, 8.1) and can be loaded in tension via at least one force transmission (11, 6, 5, 5.1). The tensioning is applied and supported via a cable tensioning system with an integrated freewheeling and adjustment function between the lower body connection and the rigid back element 1, which is preferably held in position by a structure adapted to the natural shape of the spine and hip, stomach and upper body connections, thus the back extensor muscles—especially in the lumbar region—in the static holding work and the hip extensor muscles in the concentric and eccentric work.

It is advantageous if the power transmission can be adjusted with the simultaneous activation of the first energy storage device and participation of the freewheeling function to compensate for the asymmetrical forces. The asymmetrical forces occur if, for example, only one leg is moved forward and, as a result, a corresponding partial energy storage device is loaded on one side. In the embodiment described here, this is achieved by adjusting the working length of a tension core acting as a force transmission element in at least one hip element, which adjusts the use of force from the thigh connection via a deflection roller (6) to the partial energy storage device.

It is also advantageous if two energy storage devices which can be adjusted independently of one another—a lower/first and an upper/second energy storage device (21, 21.1 and 2)—are provided in the lifting aid and use the same freewheeling concept (length compensation of the tension cores via the rollers). In one embodiment, which is shown in the figures below, the lower/first energy storage device is divided into two (21, 21.1)—i.e., one half is located on the right thigh connection and the other half on the left thigh connection. The free end of the tension core (11) is also fastened to each of the two partial energy storage devices, so that these are tightened between the thigh connection and the back element when bending and are relaxed when standing up.

In the lifting aid according to the invention, the upper energy storage device 2, the use of which leads to a change in the system characteristics or supplements the support force with a second additional continuous force, can be optionally activated and configured by adjusting the adjustment strap 12 accordingly. When using two separate energy storage devices (lower and upper energy storage device), it makes sense to separate the respective adjustment options from each other, which is why in the lifting aid according to the invention, the amount of support from the lower/first energy storage device and the position-dependent additional power support from the upper/second energy storage device can be independently and continuously adjusted via the adjustment straps adjusting the deflection roller.

The continuous energy storage devices such as metal springs, rubber bands, elastomers and dampers that can exert the restoring forces against stretching are suitable as the spring elements. It is also favorable to be able to change the elastic behavior of the lifting aid by exchanging the respective energy storage devices (21, 21.1, 2). Accordingly, in the lifting aid according to the invention, a modular system of the energy storage devices with the different spring characteristics enables the configuration of the system behavior depending on the desired support.

It is favorable if the energy storage elements of a lifting aid do not apply an elastic counterforce against the walking movements, i.e., the slight asymmetrical leg movements by the wearer, so that the wearer is not disturbed when he/she is not performing a lifting movement. Accordingly, in one embodiment, the lifting aid has a freewheeling function for the tension core 11 via the deflection rollers 6 for the first/lower energy storage device and a freewheeling function for the tension core 11.1 via the deflection rollers 6, 3 for the second/upper energy storage device.

The known lifting aids with the adjustment mechanisms in the hip area divert the tensile forces that arise from the energy storage devices to a hip belt, whereby the large parts of the supporting force can press on the wearer's stomach area. It therefore makes sense to keep the adjustment of the energy storage elements in the hip elements free of force from the hip belt. Accordingly, the lifting aid according to the invention includes the hip elements with the flexible but longitudinally incompressible guide plates 13, which allow the supporting tensile forces of the tension cores from the energy storage devices to act on the guide plates 13 and the rigid back element 1, which are therefore not introduced into the body of the wearer.

The use of a rigid back element 1 also absorbs the forces that arise between the thigh connection and shoulder carriers due to stretching of the energy storage elements and can act as tensile and bending forces on the spine and are only applied to the specific areas of the body.

The lifting aid is easy and unproblematic to put on due to its simple structure and supports the back muscles of the wearer when bending over with the loads through the stabilization and the hip extensor muscles through the supporting tensile forces when lifting. The wearer is prevented from lifting with a strongly rounded back in the lumbar region and thus the harmful peak loads on the intervertebral discs are reduced, as the back element applies the part of the tensile forces as pressure on the lower back and thereby also corrects the posture. In addition, the wearer's back extensor muscles are supported during static work, which prevents the pain caused by the muscle hardening (see FIG. 10 and FIG. 11).

The invention is explained in more detail below with reference to the exemplary embodiments and the drawings, to which, however, it is in no way limited.

DETAILED DESCRIPTION OF THE INVENTION

Figure 1:
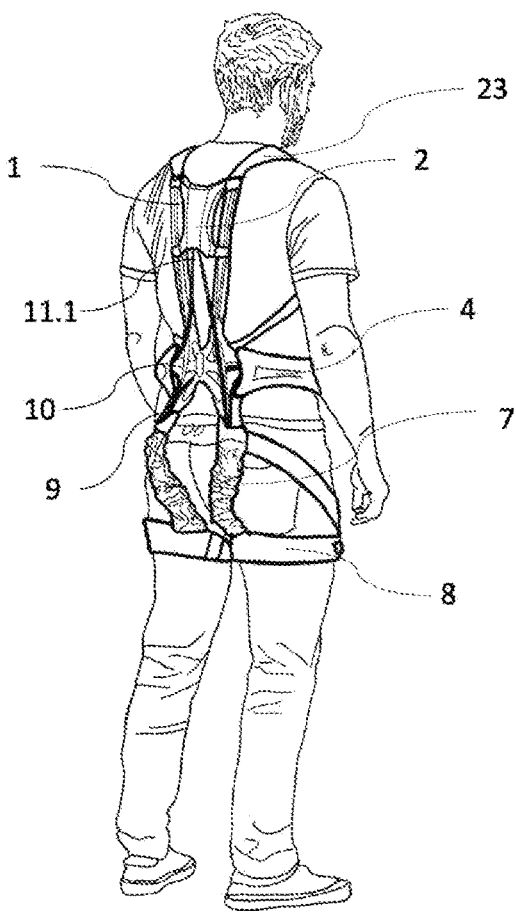
FIG. 1 is a perspective view of a rear view of a lifting aid worn by a person.
Figure 2:
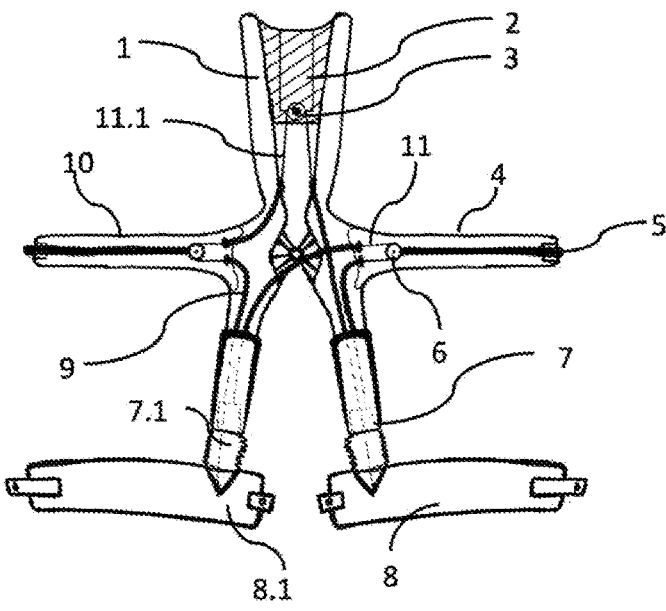
FIG. 2 shows schematically the individual elements of the lifting aid with the elastic energy storage devices in the non-applied state from the rear view.

The lifting aid (FIG. 1) with the shoulder carriers as the upper body connection 23, the two-part waist belt 17 and the lower body connection (here the thigh connections (8, 8.1)), with a rigid back element 1 arranged in between on the body and the hip elements 10, 4, the energy storage devices 21 and the force transmissions (here tension cores 11, 11.1), controls the force application of the energy storage devices and is intended to support the wearer in his posture during lifting and through the elastic spring force in the lifting movement. The support is provided by a direct posture correction against a hunchback and sloping lifting as well as a support is provided by the tensile force depending on the bending angle of the hips by the continuous energy storage device—here the spring elements 21, 21.1, 2.

The bending (respectively reducing the hip flexion angle) lengthens the path of the tension cores 11, 11.1 in the connecting jackets 7,7.1 between the back element 1 and the thigh connections 8, 8.1, which stress the energy storage devices for stretching and at the same time build up the restoring forces.

In the embodiment of FIGS. 1-8, a divided lower/first energy storage device 21, 21.1 and an upper/second energy storage device 2 are installed. These can be equipped with the elastomers, springs and other materials that exert an elastic restoring force when stretched, wherein a combination of the spring elements is also possible which, when subjected to tension, continuously apply a tensile force in proportion to the elongation.

The rigid back element 1 of the lifting aid, which connects the hip elements 4, 10 and the energy storage devices 21, 21.1 and 2 and directs the tension core(s) 11, 11.1, is stable in itself. It absorbs the forces from the tension cores and the deflection rollers 6 during adjustment on the guide plates 13 in the hip elements 4, 10 and the upper freewheel roller 3 and dissipates them into the material. Some of the forces act as postural pressure on the lower back.

The lifting aid (FIG. 2) includes two separate energy storage devices—an upper energy storage device (2) and a lower (divided) energy storage device (21, 21.1). Both energy storage devices are continuously adjustable via the freewheel roller 3 for the tension core 11.1 and a freewheel roller 6 for the tension core 11.

The lower/first energy storage system consists of the right and left partial storage devices (21, 21.1), which are fixed to the right and left thigh connection (8, 8.1), the tension core 11 attached to the partial energy storage devices, and the adjustment and freewheeling device in the right hip element 4, comprising a deflection roller 6, the adjustment strap 5 and the adjustable clamping device 5.1.

The upper/second elastic energy storage device 2 is connected to the freewheel roller 3, wherein the second tension core 11.1, which is fixed to the connection points 22, 22.1 on the thigh connections 8, 8.1, is deflected on the freewheel roller 3 and pulls it downward against the spring force of the second energy storage device.

Figure 3:
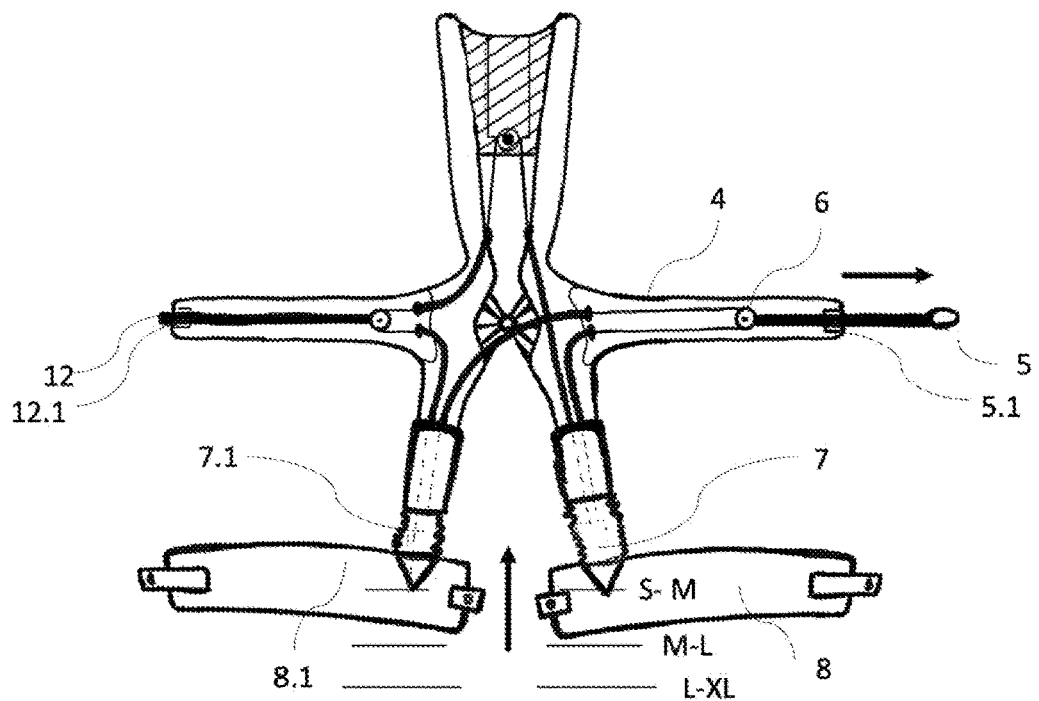
FIG. 3 shows schematically the individual elements of FIG. 2 during the activation and adjustment of lower partial energy storage devices.

FIG. 3 shows a change in support by the first energy storage system. This is done by pulling the adjustment strap 5 guided in the right hip element, which causes it to move further through the open clamping device 5.1. The adjustment strap 5 is then fixed in position by closing the clamping device 5.1. The adjustment is continuous but can also be implemented in the defined adjustment steps using a conventional buckle with a pin. By moving the adjustment strap 5, the freewheel roller 6 guided on the guide plate 13 in the guide liner 14 is displaced and the effective length of the tension core 11 between the thigh connections 8, 8.1 and the back element 1 is thus shortened. The guide liner 14 causes a reduction in the friction between the tension core 11 and the jacket 15 of the right hip element 4, which envelops the tensioning cable system there and holds it together. The shortening of the effective length of the tension core 11 causes a stronger support force that begins to take effect even from a smaller hip angle of <180° (this corresponds to standing upright).

Regardless of the setting of the support force of the first elastic storage device 21, 21.1, the freewheeling function is maintained via the upper freewheel roller 3. The tensile forces applied by the energy storage devices 7, 7.1 are not transferred to the waist belt 17, but rather are introduced into the material of the rigid back element 1 along the guide plate 13, which is incompressible in the longitudinal direction, when the waist belt closure is closed.

Figure 4:
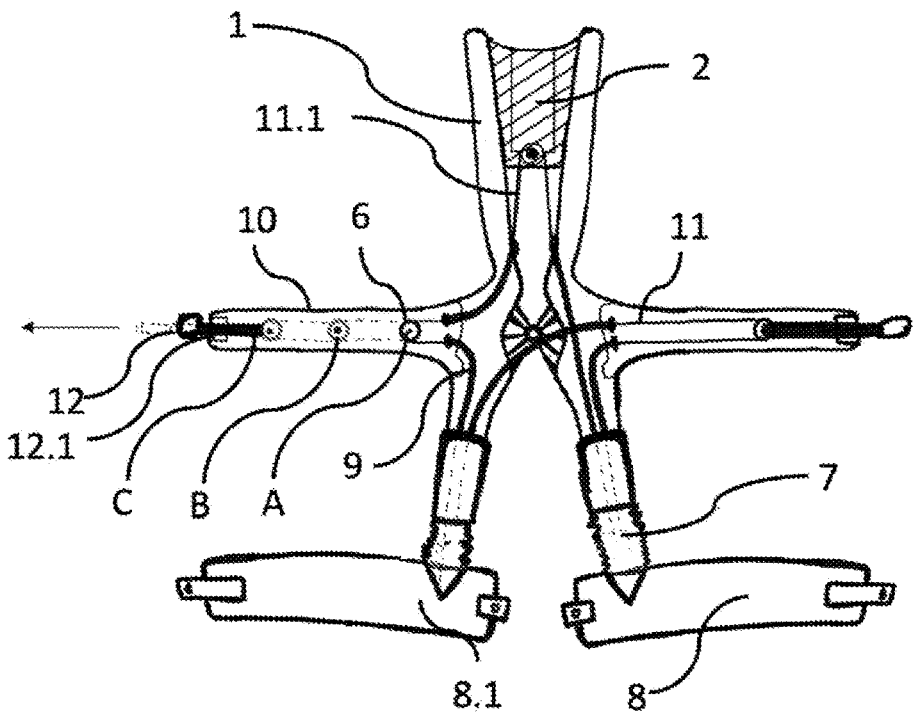
FIG. 4 shows schematically the individual elements from FIG. 2 and FIG. 3 during the activation and adjustment of the second energy storage devices.

The same functional principle applies to the setting of the second energy storage device 2, the effect of which is also continuously adjustable via the belt 12 in the left hip element 10 and—in this embodiment—a clamping device 12.1 (FIG. 4). The course of the second tension core 11.1 over the deflection roller 6 in the hip element 10 and the upper freewheel roller 3 enables the freewheeling function independently of the support force setting. Of course, the buckles with a pin can also be used for setting and fixing the deflection roller 6 guided on the guide plate 13 for the second tension core 11.1 instead of a clamping device.

Figure 6:
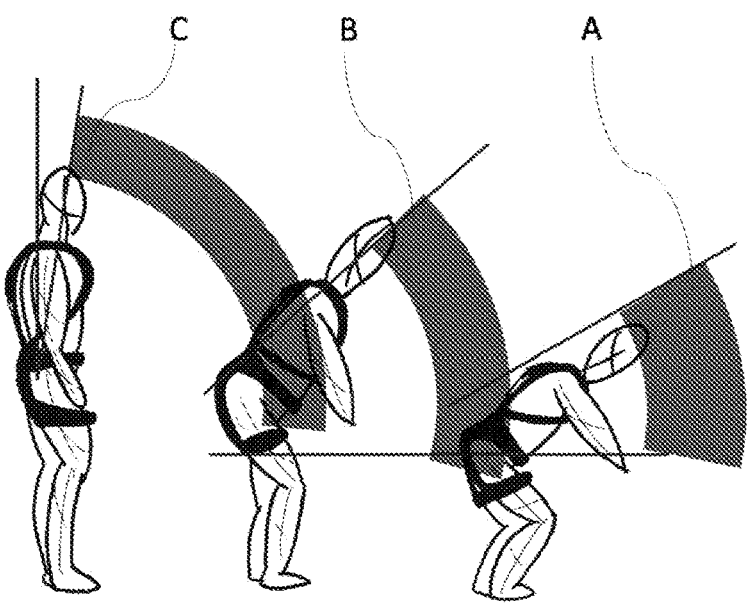
FIG. 6 shows schematically some static working positions.
Figure 7:
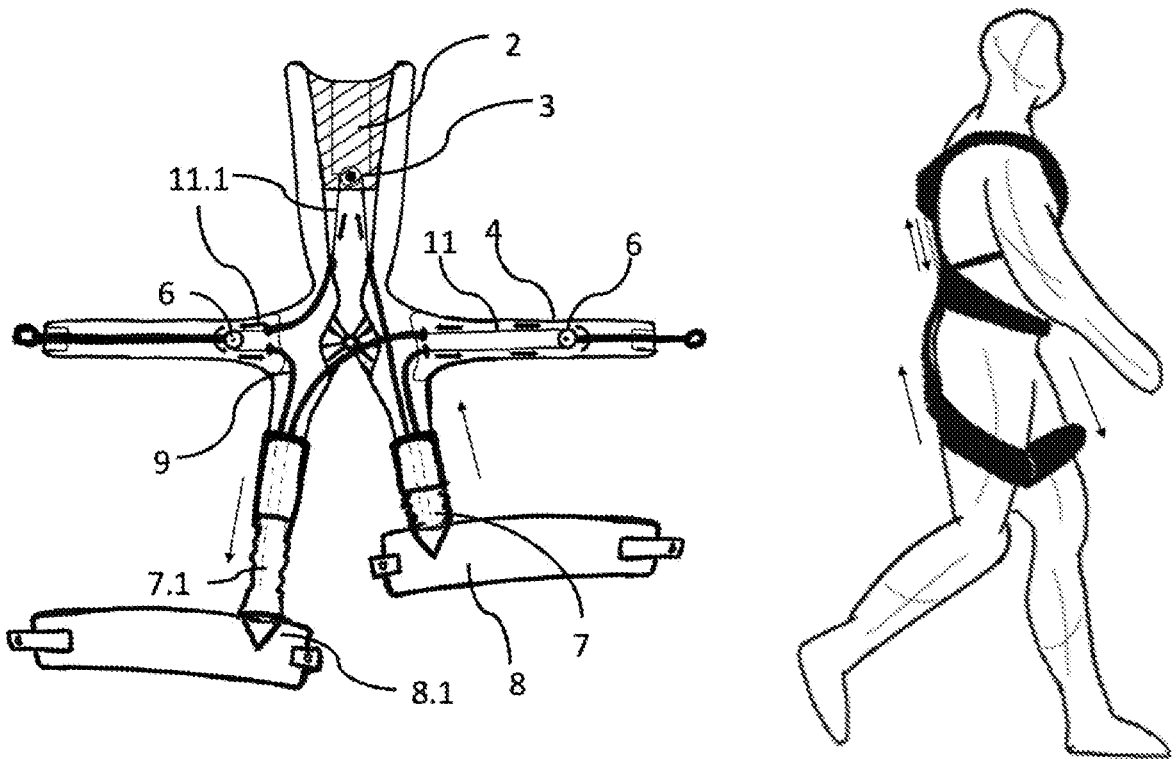
FIG. 7 shows schematically the individual elements of the lifting aid when walking and a rear view of the wearer.
Figure 8:
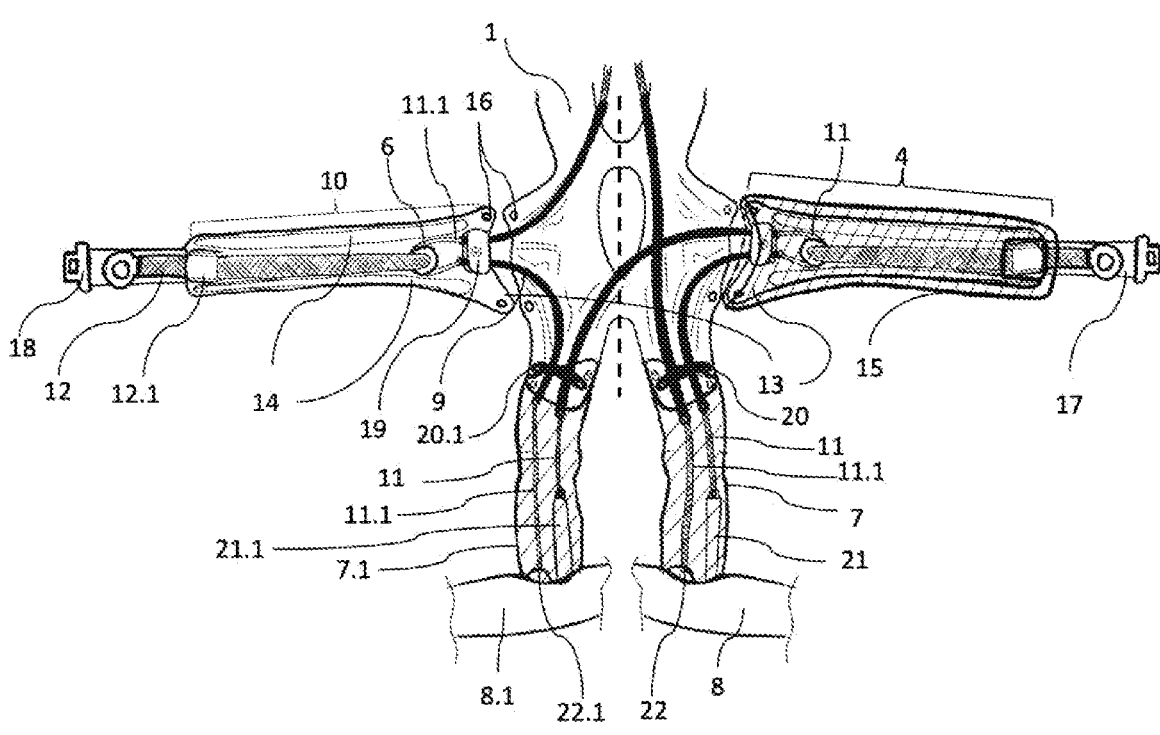
FIG. 8 shows a detailed view of the hip module/waist belt area with the lower partial energy storage devices of the lifting aid.

FIG. 6 shows the different settings in relation to the adjustment of the second energy storage device 2, which causes a change in the support force and its effect as a function of the bending angle. That is, depending on the position of the deflection roller 6 in the left hip module 10, the support force of the second support element 2 acts earlier (strong support, Example C) or later (weak support, Example A) when bending.

The ability to set an additional energy storage device 2 that is provided separately from other energy storage devices (21, 21.1) is unique and opens many additional setting options for the wearer by combining the two energy storage systems. In this way, the complete system characteristics can be changed. The additional support force of the second energy storage device 2 is added to the basic support of the first energy storage system by the elastic energy storage devices 21, 21.1. Through the individual setting and the additional activation, the wearer can adapt the system to suit their own preferences and the work environment. This enables a high level of wearing and application comfort.

The setting of the support force of the two energy storage devices via only one adjustment strap 5, 12 each and the associated clamping device 5.1, 12.1 enables quick and easy adjustment before and between the lifting activities. The setting is made symmetrically for the left and right half of the body for the respective energy storage system in order to prevent the asymmetrical loads on the body from the lifting aid. The right clamping device 5.1 is responsible for the first energy storage device 21, 21.1 and the left clamping device 12.1 is responsible for the second energy storage device 2 for switching off/releasing the support from the energy storage device and can be easily adjusted and released.

Figure 5:
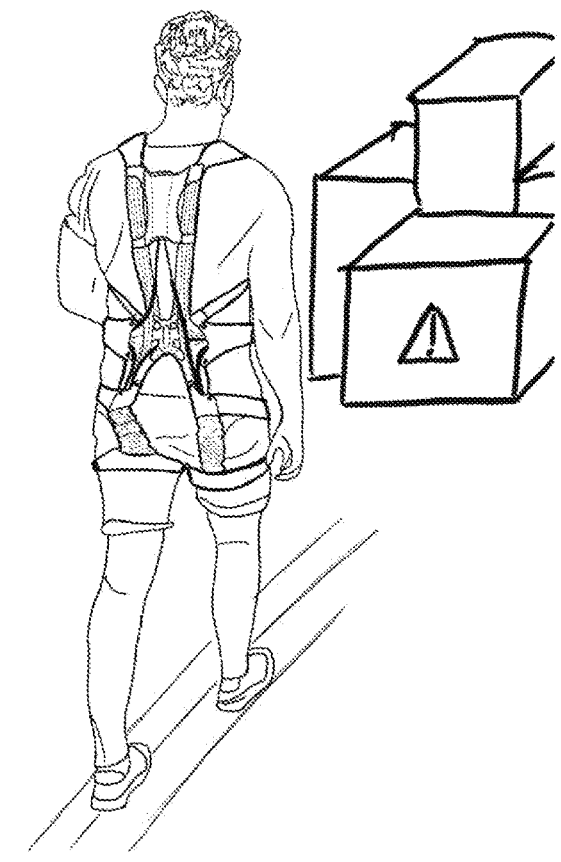
FIG. 5 shows schematically a perspective view of a wearer with a lifting aid using the freewheeling function when walking.

It can be seen in FIG. 5 that the walking movement causes one-sided changes in the hip angle, which affect the energy storage devices 21, 21.1 in the connecting jackets 7, 7.1. Without a freewheel device 6, this would have the effect of stretching the energy storage devices 7, 7.1, which would then apply an asymmetrical tensile force and thus restrict the running movement. The system according to the invention with an upper and lower energy storage device enables the setting of two supports that can be activated separately from one another. If these always had to be deactivated when running, the acceptance by the wearers would drop sharply.

Therefore, the lifting aid (FIG. 7) includes an integrated freewheeling function, which is independent of any setting in the system, since the tension cores 11, 11.1 are adjusted and compensated accordingly when running via deflection rollers 6, 3. The freewheeling function is activated by the asymmetrical movement of the legs, e.g., when running, while it remains inactive with symmetrical bending, whereby the energy storage systems can apply the support power. The entire functional principle is mechanical and does not require any electrical control. The tension cores 11,

11.1 moving through the system as a result of the freewheeling function are guided in the guiding jackets 9 with the low-friction guide liners 14 in the hip elements 4, 10 on the guide plates 13 which are also low-friction. As a result, the wearer is only minimally affected.

The tension cores 11, 11.1 are guided with little friction in the guiding jackets 9 on the guide plates 13, which are incompressible in the longitudinal direction but are flexible and are deflected via the deflection rollers 6 and 3. As a result, the tension cores 11, 11.1 remain flexible. The guide liner 14 weakens the friction of the tension cores through a special material adjustment on the guide plates and the guide jacket, so that they are almost friction-free. The brushes or low-friction plastic linings, for example, are suitable for this. If the wearer moves a leg, all of the tension cores 11, 11' attached at one end to the thigh connections 8, 8.1 also move in the entire system. This reduces the restriction of the wearer from the tension core when walking to an imperceptible level.

Figure 9:
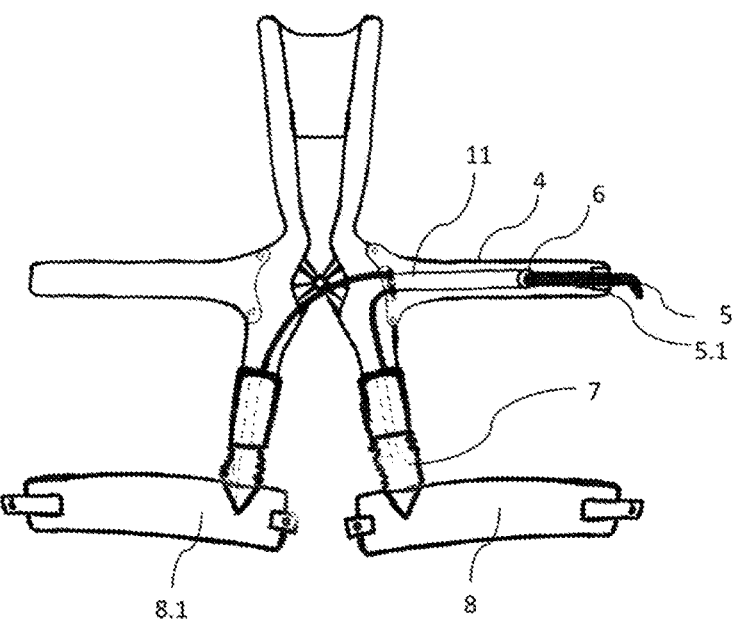
FIG. 9 shows a rear view of a simple embodiment of the lifting aid with the lower partial energy storage devices.

A simpler embodiment of the invention is shown in FIG. 9, which has only one tension core 11 and only one adjustability in the right hip module 4 with the freewheel roller 6, the adjustment strap 5 and adjustable clamping device 5.1. The second energy storage device is not available, whereby the left hip element has no adjusting function. The system has the functions of the first divided energy storage devices 21, 21.1, i.e., a freewheeling function and posture and movement support.

Figure 10:
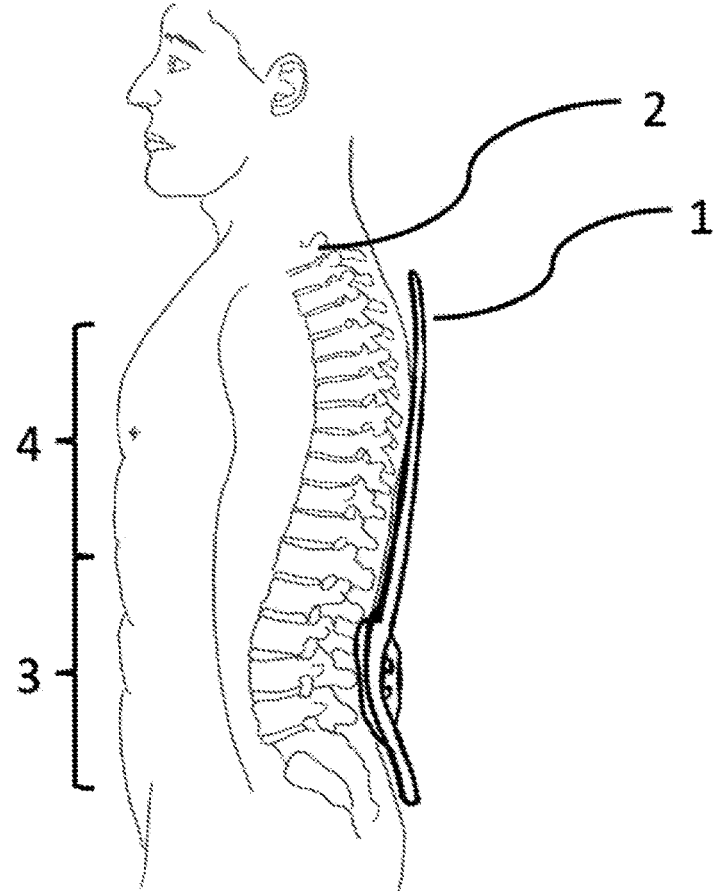
FIG. 10 shows a schematic view of the spine with the back element lying thereon.
Figure 11:
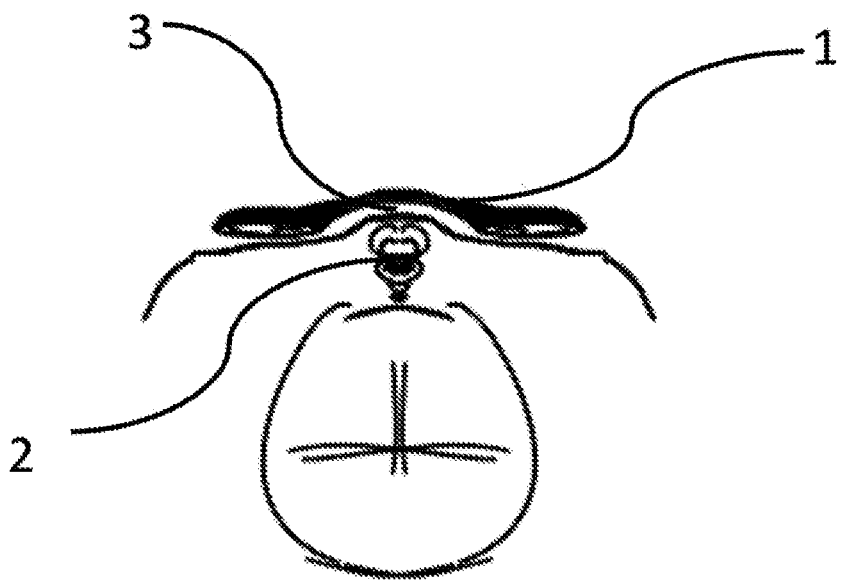
FIG. 11 shows a schematic view of a cross section through the trunk with a vertebral body with a back element lying thereon.

FIG. 10 shows the support of the back element in the region of the lumbar spine up to the first ribs and the sacrum. In this area, the back element attached to the body exerts the restoring forces against bending of the torso and thus prevents a rounded back. In particular, since the relatively rigid back element preferably has a recess for receiving the spinous processes of the vertebral bodies, it is prevented from the lateral displacement and thus also acts as an obstacle to a sideways movement of the spine that puts strain on the intervertebral discs, as shown in FIG. 11, that a shaped part corresponding to the optimum spinal posture, the minimum length of which is from the lumbar vertebra 2 or 3 to the thoracic vertebra 7, the maximum is the distance from the sacrum to the cervical vertebra 3 and the width of which can vary between the width of the sacrum to the width of the back, with a longitudinal recess for receiving the spinous processes of the spinal column in its side facing the back, and attachment devices for the carrying belts for attaching the back element on a person.

The back elements are generally suitable for back training or the prevention of incorrect movements in order to limit one-sided loads and to avoid particularly stressful movements when lifting.

Typical flexural modulus values for a back element material are between 500-100000 MPa, preferably between 800 to 5000 and particularly preferably between 1500 and 3000 mPa. Layered materials, such as wood laminates or composite materials made up of layers, plastics, but also metal plates—for example made of aluminum—can be suitable.

While the invention has been described with reference to the exemplary embodiments, these embodiments are by no means intended to describe all possible forms of the invention. The expressions in the description are purely descriptive, not restrictive, and it is understood that a wide variety of variations are possible without departing from the spirit and scope of the invention. Additionally, the features of the embodiments may be combined to form further embodiments.

7

Reference Numeral List

1 Back element
2 Second elastic energy storage device
3 Freewheel roller
4 Right hip element
5 Adjustment straps of 4
5.1 Adjustable clamping device of 4
6 Deflection roller/Freewheel roller in hip element 4, 10
7 Right connecting jacket for tension cores (11, 11.1) and spring element (21) between back element 1 and right thigh connection (8)
7.1 Left connecting jacket for tension cores (11, 11.1) and spring element (21.1) between back element 1 and left thigh connection (8.1)
8 Right thigh connection
8.1 Left thigh connection
9 Guiding jacket of the tension core(s) 11, 11.1
10 Left hip element
11 First tension core of the first energy storage device
11.1 Second tension core of the second energy storage device
12 Adjustment straps in 10
12.1 Adjustable clamping device in 10
13 Guide plate(s) in hip element(s) for core(s) (11, 11.1)
14 Guide liner in 15
15 Jacket for hip elements 4, 10
16 Attachment point from 13 to 1
17 Waist belt in 4
18 Waist belt buckle on 17
21 Right energy storage device in 7
21.1 Left energy storage device in 7.1
22 Connection point of the tension core 11.1 to 8
22.1 Connection point for tension core 11.1 to 8.1
23 Upper body connection (shoulder carriers)
A Setting position for support for deep bending
B Setting position for support in medium bending
C Setting position for support from slight bending

The invention claimed is:

1. A lifting aid for supporting trunk muscles of a person on which the aid is arranged, comprising:
an upper connection and a lower body connection,
a fixed back system with right and left hip elements hinged thereto,
at least one mechanical energy storage device for tensioning energy having at least one adjustable lower energy storage device with spring elements which are attached at one end to the lower body connection,
at least one force transmission element/tensioning device which is attached to the lower energy storage device and connects it to the fixed back system, and
freewheel devices with freewheeling and adjustment functions in the hip elements,

wherein, when the fixed back system is fixed to a person's back, tensile forces of the energy storage devices are transmitted to an area of the person's back,
further comprising an upper energy storage device which is adjustable independently of the lower energy storage device and which is connected to the lower body connection and activated via a second tension element and uses an upper freewheel roller.

2. The lifting aid according to claim 1, wherein the hip elements have a tension element adjustment for changing activation of the at least one lower energy storage device and the freewheeling function.

3. The lifting aid according to claim 1, wherein the lower energy storage device is divided in two and is attached to the lower body connection.

4. The lifting aid according to claim 1, wherein at least one of the energy storage devices is constructed to continuously absorb and deliver force.

5. The lifting aid according to claim 1, further comprising two mutually separate setting elements for setting the degree of support of the upper and lower energy storage devices.

6. The lifting aid according to claim 1, further comprising at least one energy transmission/tension core for power transmission via the freewheel device.

7. The lifting aid according to claim 1, wherein the fixed back system is constructed to be able to absorb forces from the mechanical energy storage devices and to redistribute and dissipate the forces to the specific locations.

8. The lifting aid according to claim 1, wherein the lifting aid is a medical lifting aid for caregivers.

9. The lifting aid according to claim 7, wherein the lifting aid is a carrying support for a construction worker or moving worker, or logistics worker.

10. The lifting aid according to claim 1, wherein, for posture support, the fixed back system has a fixed back element with a shaped part corresponding to optimum spinal posture with a minimum length of from a wearer's lumbar vertebra 2 or 3 to the wearer's thoracic vertebra 7, and a maximum distance from the wearer's sacrum to the wearer's cervical vertebra 3 and the width of which can vary between the width of the wearer's sacrum to the width of the wearer's back, and with a longitudinal recess for receiving spinal column spinous processes in a back facing side, and attachment devices for carrying belts for attaching the back element on a person.

11. The lifting aid according to claim 10, wherein the fixed back element has a flexural modulus of 500 to 80 000 Mpa.

12. The lifting aid according to claim 10, wherein the fixed back element has a flexural modulus of 1000-50 000 Mpa.

13. The lifting aid according to claim 10, wherein the fixed back element has a flexural modulus of between 1500 and 10 000 Mpa.

14. The lifting aid according to claim 10, wherein the fixed back element essentially comprises a part formed of a material from one of a fiber-reinforced plastic, a plastic or wood laminate, a layered material or a metal alloy.

* * * * *